United States Patent
Jbach

(10) Patent No.: US 10,035,748 B2
(45) Date of Patent: Jul. 31, 2018

(54) METHOD FOR CATALYTIC GENERATION OF FORMIC ACID AT AN OXYGEN PARTIAL PRESSURE BELOW 1 BAR AND REGENERATION OF THE CATALYST USED THEREFOR

(71) Applicant: OXFA GMBH, Schesslitz (DE)

(72) Inventor: Hermann Wolf Jbach, Bischberg (DE)

(73) Assignee: OXFA GMBH, Schesslitz (DE)

( * ) Notice: Subject to any disclaimer, the term of this patent is extended or adjusted under 35 U.S.C. 154(b) by 0 days.

(21) Appl. No.: 15/544,857

(22) PCT Filed: Jan. 22, 2016

(86) PCT No.: PCT/EP2016/051348
§ 371 (c)(1),
(2) Date: Jul. 19, 2017

(87) PCT Pub. No.: WO2016/120169
PCT Pub. Date: Aug. 4, 2016

(65) Prior Publication Data
US 2018/0022678 A1    Jan. 25, 2018

(30) Foreign Application Priority Data
Jan. 26, 2015 (EP) .................................... 15152518

(51) Int. Cl.
*C07C 51/235* (2006.01)
*C07C 53/02* (2006.01)

(52) U.S. Cl.
CPC ............ *C07C 51/235* (2013.01); *C07C 53/02* (2013.01)

(58) Field of Classification Search
CPC .................................................... C07C 51/23
See application file for complete search history.

(56) References Cited

U.S. PATENT DOCUMENTS 5,695,606 A * 12/1997 Weinstock et al. .. D21C 9/1057
162/79
2013/0245319 A1 * 9/2013 Bosmann ................ C07C 51/23
562/531

FOREIGN PATENT DOCUMENTS

| EP | 0090128 A1 | 10/1983 |
|---|---|---|
| EP | 2473467 B1 | 9/2013 |
| JP | 2008-273915 A | 11/2008 |
| WO | 2016078698 A1 | 5/2016 |

OTHER PUBLICATIONS

International Search Report dated Mar. 30, 2016, in PCT/EP2016/051348 (ISR 2 pages, English translation 2 pages).

* cited by examiner

*Primary Examiner* — Paul A Zucker
(74) *Attorney, Agent, or Firm* — Prismatic Law Group, PLLC; Ronald J. Kamis

(57) ABSTRACT

Methods for catalytic generation of formic acid at an oxygen partial pressure of less than 1 bar and regeneration of the catalyst used in this process, wherein a polyoxometallate ion of the general formula $[PMo_xV_yO_{40}]^{n-}$, which serves as the catalyst, is brought in contact with an alpha-hydroxyaldehyde, an alpha-hydroxycarboxylic acid, a carbohydrate, a glycoside or a polymer containing a carbon chain with at least one OH group bound as a repeatedly occurring substituent to the carbon chain and/or an O, N or S atom occurring repeatedly in the carbon chain in a liquid solution in a vessel, at a temperature above 70 ° C. and below 120 ° C.

20 Claims, 2 Drawing Sheets

Figure 1:
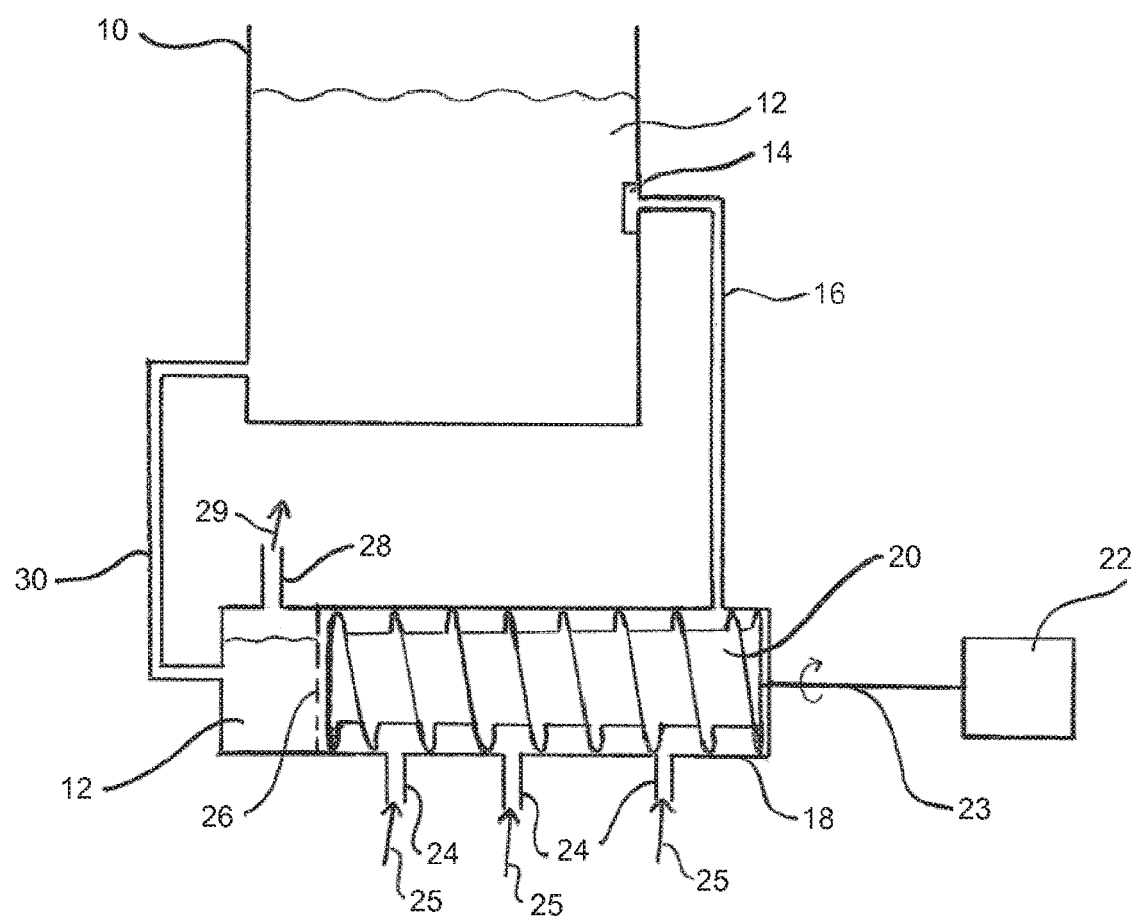

METHOD FOR CATALYTIC GENERATION OF FORMIC ACID AT AN OXYGEN PARTIAL PRESSURE BELOW 1 BAR AND REGENERATION OF THE CATALYST USED THEREFOR

The present invention is filed under 35 U.S.C. § 371 as the U.S. national phase of International Patent Application No. PCT/EP2016/051348, filed Jan. 22, 2016, which designated the United States and which claims priority to European Patent Application No. 15152518.5 filed Jan. 26, 2015, each of which is hereby incorporated in its entirety including all tables, figures and claims.

The invention relates to a method for catalytic generation of formic acid and regeneration of the catalyst used therein. Such a method is known from EP 2 473 467 B1, wherein a polyoxometallate ion of the general formula $[PMo_xV_yO_{40}]^{5-}$, which serves as the catalyst is brought into contact with an alpha-hydroxyaldehyde, an alpha-hydroxycarboxylic acid, a carbohydrate or a glycoside in a liquid solution at a temperature above 70° C. and below 120° C. in a vessel, wherein $6<x<11$ and $1<y<6$ and $x+y=12$, wherein x and y are each integers. The catalyst thereby reduced is returned to its starting state by oxidation.

According to EP 2 473 467 B1, it is advantageous if the contacting takes place under an oxygen partial pressure of 1 to 500 bar. The higher the oxygen partial pressure, the more rapid is the oxidation of the catalyst, which becomes reduced in this process. However, it has now been found that the pressure vessels made of steel that are used to carry out this process develop heavy corrosion. To avoid this, highly corrosion-resistant but relatively expensive nickel-chromium-molybdenum alloys, such as the so-called "Hastelloy C" from the company Haynes International, Inc., Kokomo, USA, can be used. If the vessel is made of such an alloy, it becomes relatively expensive to carry out this process. The object of the present invention is therefore to provide a less expensive option for carrying out this process.

This object is achieved through the features of patent claim 1. Expedient embodiments are derived from the features of patent claims 2 to 15, According to the invention, a method for catalytic generation of formic acid at an oxygen partial pressure of less than 1 bar and for regeneration of the catalyst used in this process is provided, wherein a polyoxometallate ion of the general formula $[PMo_xV_yO_{40}]^{n-}$ is brought in contact with an alpha-hydroxyaldehyde, an alpha-hydroxycarboxylic acid, a carbohydrate, a glycoside or a polymer containing a carbon chain with at least one OH group bound repeatedly to the carbon chain as a substituent and/or with an O, N or S atom occurring repeatedly in the carbon chain, in a liquid solution in a vessel at temperatures above 70° C. and below 120° C., wherein $6\leq x\leq 11$ and $1\leq y\leq 6$ and $3<n<10$ and $x+y=12$, wherein x and y each are integers. In one embodiment of the method, $n=3+y$. The charge may also assume other values from 4 to 9, depending on the conditions in the reaction mixture, such as the pH.

The catalyst, which is reduced to form the formic acid in this reaction, is returned to its starting state by oxidation. In the sense of the invention, a catalyst is thus also understood to be a substance that changes due to reduction during the process and is returned to its starting state by oxidation. The contacting takes place at an oxygen partial pressure of less than 1 bar in the vessel. For oxidation of the catalyst, some of the liquid solution is discharged out of the vessel, exposed to oxygen or a gas mixture containing oxygen at an oxygen partial pressure of 1 to 500 bar, in particular 5 to 500 bar, in particular 10 to 500 bar, and then returned to the remainder of the liquid solution. In doing so, the oxygen partial pressure in the vessel is always kept below 1 bar. To do so, the oxygen partial pressure acting upon that portion of the liquid solution is reduced from 1 to 500 bar to a value of less than 5 bar, in particular less than 1 bar, before that portion of the liquid solution is returned to the remainder of the liquid solution.

It is possible that the portion of the liquid solution under an oxygen partial pressure of less than 5 bar, in particular less than 1 bar, is supplied to the remainder of the liquid solution at a pressure higher than the pressure which the remainder of the liquid solution is under. In doing so, the portion of the liquid solution that is supplied is degassed because of the lower pressure to which the remainder of the liquid solution is exposed. To prevent an increase in pressure to 1 bar or more, the gas escaping from the liquid must be allowed to escape from the vessel in a sufficient amount. Supplying that portion of the liquid solution, which is under a higher pressure than the remainder of the liquid solution, to the remainder of the liquid solution at this pressure can also be configured as an influx of that portion of the liquid solution into the remainder of the liquid solution and utilized to achieve a thorough mixing of the liquid solution because of the pressure difference between that portion of the liquid solution and the remainder of the liquid solution. The influx may take place through suitably designed nozzles, in particular nozzles that can be varied in the direction of flow and/or in the outlet diameter. By varying the outlet diameter, the outflow velocity of that portion of the liquid solution out of the nozzle can be varied.

The gas mixture containing oxygen may be air, for example. The gas mixture may contain more than 10 vol % oxygen. The exposure to the oxygen or the gas mixture may take place for example by injecting the oxygen or the gas mixture into that portion of the liquid solution.

The solution may comprise a solvent. It is not necessary to provide a solvent if the alpha-hydroxyaldehyde, the alpha-hydroxycarboxylic acid, the carbohydrate, the glycoside or the polymer is already in liquid form. An alpha-hydroxyaldehyde is understood to be a molecule in which an OH group is bound directly to a C atom, wherein the C atom of an aldehyde group is also bound directly to the C atom. An alpha-hydroxycarboxylic acid is understood to be a molecule in which an OH group is bound directly to a C atom, where the C atom of a carboxy group is also bound directly to the C atom. An alpha-hydroxyaldehyde and an alpha-hydroxycarboxylic acid may also each be understood to be a substance which contains an alpha-hydroxyaldehyde or an alpha-hydroxycarboxylic acid, respectively.

The inventors of the present invention have recognized that the corrosion of a steel vessel used to carry out the process known from EP 2 473 467 B1 is greatly promoted by the interaction of the elevated oxygen partial pressure and a temperature higher than 70° C. and lower than 120° C. They have also recognized that, for effective oxidation of the reduced catalyst, it is not necessary for the exposure to oxygen or a gas mixture containing oxygen to take place at an oxygen partial pressure of 1 to 500 bar at a temperature above 70° C. and below 120° C.

The method according to the invention makes it possible to cool that part of the liquid solution and then expose it to the elevated oxygen partial pressure, so that, in this way, another vessel that contacts that portion of the liquid solution during the exposure to the oxygen or the gas mixture containing oxygen is not therefore subject to a greatly increased corrosion. Alternatively, the cooling step may also be omitted, and then only a relatively small additional vessel may be used for the exposure to the oxygen or the gas mixture. The relatively high cost of a highly corrosion-resistant material is not as significant as for a relatively small additional vessel as would be the case when providing a relatively large vessel made of such a highly corrosion-resistant material in which the catalytic reaction with the alpha-hydroxyaldehyde, the alpha-hydroxycarboxylic acid, the carbohydrate or the glycoside takes place. The vessel in which the catalytic reaction takes place can be made of a very inexpensive material. It may even be open at the top because the catalytic reaction can also take place at atmospheric pressure. Therefore, the vessel need not be pressure-resistant.

To retain the solids distributed in the liquid, when a portion of the liquid solution is discharged out of the vessel, a filter may be provided to retain the solids. Such a filter can prevent solids from entering the downstream portion of the device for carrying out the process and may cause clogging of the valves or other parts of the device there or otherwise interfere with their function.

In one embodiment of the method according to the invention, the alpha-hydroxyaldehyde, the alpha-hydroxycarboxylic acid, the carbohydrate, the glycoside or the polymer is present in the liquid solution in the form of solids distributed therein. These solids may be finely distributed or coarsely distributed in the liquid solution.

The polymer may be a polyester, a polyamine or a polyimide, in particular polyhexamethylene adipamide (nylon). The polymer may be a polymer without a plasticizer. Plasticizers can have a negative effect on the activity of the catalyst.

Alpha-hydroxyaldehydes, alpha-hydroxycarboxylic acids, carbohydrates and glycosides occur in a large number of renewable raw materials, such as starch, cellulose or hemicellulose, for example. Cellulose and hemicellulose are obtained in large quantities as by-products of crop plants or in industrial digestion of wood for making paper, for example.

The alpha-hydroxyaldehyde, alpha-hydroxycarboxylic acid, carbohydrate or glycoside may be a monosaccharide, in particular an aldose, disaccharide, oligosaccharide or polysaccharide, starch, cellulose, hemicellulose, glucose, sucrose, xylose, cellobiose, xylan, a hetero-oligosaccharide, a heteropolysaccharide, glycolic acid or lactic acid or a residual material or raw material that contains the alpha-hydroxyaldehyde, alpha-hydroxycarboxylic acid, carbohydrate or glycoside or in particular renewable raw materials, in particular those that are untreated. "Untreated" here means that the raw material has not first been chemically digested. The residual material or the renewable raw material may be a plant, a fungus or bacteria or components of plants, fungi or bacteria, wood, in particular in the form of sawdust or wood shavings, paper, in particular waste paper, scrap paper and recycled paper, algae, cyanobacteria or silage. The alpha-hydroxyaldehyde, alpha-hydroxycarboxylic acid, carbohydrate or glycoside may also be present in the form of a mixture of at least two of the aforementioned substances or at least one of the aforementioned substances or a mixture, as is the case with lignite or peat, for example.

Many of the aforementioned raw materials are obtained as by-products, for example, in papermaking or in wood processing. They are thus available as an inexpensive starting material for the method according to the invention. The method according to the invention can therefore be carried out very inexpensively. Therefore, the oxidation of the catalyst that is reduced in the catalytic reaction (=reoxidation) also contributes to this and allows the catalyst to remain in use for a very long time.

The contacting in the vessel may take place at atmospheric pressure, wherein the gas pressure in the vessel is always kept at atmospheric pressure. Therefore, the vessel can be provided very inexpensively because it need not withstand an elevated pressure. It may be a plastic vessel, for example, which can withstand a temperature above 70° C. and below 120° C. The corrosion problems mentioned above do not occur with such a plastic vessel. Atmospheric pressure is understood to be the pressure of air prevailing when the process is carried out in the surroundings of the vessel outside of a building at the same altitude above sea level at which the process is carried out.

In the vessel, the solution may be reacted at an oxygen partial pressure of less than 1 bar, in particular at atmospheric pressure, over a period of hours, days or even weeks. It is not necessary to limit the contact time with the vessel to prevent corrosion of the vessel.

To keep the gas pressure in the vessel always at atmospheric pressure, the vessel may have an opening that leads to the outside, for example, by simply having open at the top. To prevent any formic acid that is formed from escaping from such a vessel in vapor form through this opening, the vessel may have a condensation device at the opening, at which any formic acid vapor that is formed can condense, so that any condensate thereby formed can simply drip back or run back into the vessel.

Oxidation of the catalyst in that part of the liquid solution may take place within a few minutes or even seconds. For example, it is possible to expose the liquid solution to the oxygen or the gas mixture at an oxygen partial pressure of 1 to 500 bar for at most 10 minutes, in particular at most 5 minutes, in particular at most 2 minutes, in particular at most 1 minute, in particular at most 40 seconds, in particular at most 30 seconds, in particular at most 20 seconds, in particular at most 10 seconds, in particular at most 5 seconds.

That part of the liquid solution may be discharged from the vessel continuously or in intervals, in particular at regular intervals, oxidized at an oxygen partial pressure of 1 to 500 bar and then fed back to the remainder of the liquid solution either continuously or at intervals, in particular at regular intervals. The oxidation may also take place continuously or in intervals, in particular at regular intervals. This makes it possible to provide the catalyst contained in the vessel in sufficient amount during the entire process, in particular in oxidized form and thus in a form for conversion of the alpha-hydroxyaldehyde, alpha-hydroxycarboxylic acid, carbohydrate, glycoside or polymer of a suitable form without having to use a very large amount of the relatively expensive catalyst. For example, to carry out the oxidization in intervals, it is possible to introduce a portion of the liquid solution into another vessel, to inject the oxygen or the gas mixture into that part of the liquid solution there and then to expose that part of the liquid solution by means of a hydraulic press, for example, to an oxygen partial pressure of 1 to 500 bar for up to 5 minutes. Then that portion of the liquid solution can be discharged out of the additional vessel after releasing the pressure and fed back to the remainder of the liquid solution.

The entire process may also be carried out continuously or in intervals, in particular at regular intervals. To do so, for example, another portion of the liquid solution may be discharged from the vessel at intervals, in particular at regular intervals, while the formic acid contained therein, for example, in the form of a formate, and the remaining portion of the liquid solution may be fed back to the remainder of the liquid solution. A suitable process for doing so is described for example in the as yet unpublished International Patent Application PCT/EP2014/074930.

In another embodiment of the method according to the invention, that portion of the liquid solution is cooled before being exposed to the oxygen, or the gas mixture, and is exposed to the oxygen partial pressure of 1 to 500 bar at a temperature of max. 95° C., in particular max. 85° C., in particular max. 75° C., in particular max. 65° C., in particular max. 55° C., in particular max. 45° C., in particular max. 35° C., in particular max, 25° C. The greater the cooling of the portion of the liquid solution and the lower the temperature at which that portion of the liquid solution is exposed to the oxygen partial pressure of 1 to 500 bar, the lower are the corrosion resistance requirements of the material of an additional vessel in which the exposure to the oxygen or the gas mixture takes place. The cooling may take place by means of a heat exchanger, which makes it possible to supply the heat withdrawn from the portion of the liquid solution to that portion of the liquid solution before it is returned to the remainder of the liquid solution. This may be accomplished with the help of a heat pump, for example.

That portion of the liquid solution can be pumped by means of at least one pump, in particular a high-density solids pump. The pumping can take place before and/or after the exposure to the oxygen partial pressure of 1 to 500 bar. A high-density solids pump makes it possible to pump that portion of the liquid solution without having to filter out the solids distributed in the liquid solution, That portion of the liquid solution may be exposed to the oxygen partial pressure of 1 to 500 bar in another vessel. The additional vessel may therefore be designed to be relatively small. A method known from EP 0090128 A1 for gassing liquids is suitable for exposing that portion of the liquid solution to the oxygen partial pressure of 1 to 500 bar. Another possibility of gassing, for example, consists of having that portion of the liquid solution flow over a relatively large surface to be wetted by the solution, thereby exposing the gas mixture containing oxygen to the oxygen partial pressure of 1 to 500 bar. The oxygen or the gas mixture containing oxygen can then flow in countercurrent to the solution.

The oxygen partial pressure of 1 to 500 bar acting on that portion of the liquid solution may be reduced to less than 1 bar, in particular to the oxygen partial pressure prevailing at atmospheric pressure, before that portion of the liquid solution is fed back to the remainder of the liquid solution.

In one embodiment of the method, the oxygen or the gas mixture is supplied to that portion of the liquid solution, the additional vessel is a housing of a screw compactor, and the oxygen partial pressure is built up due to the fact that that the portion of the liquid solution together with the oxygen or the gas mixture is compacted by means of the screw compactor. The oxygen or the gas mixture may be contained in that part of the liquid solution in the form of gas bowls. A screw compactor is an apparatus in which a conveyor screw rotating in a housing, for example, presses the liquid solution against an outlet bordered in the passage and thereby exerts a pressure on the solution. Instead of a conveyor screw, two intermeshing conveyor screws may also be provided in one housing. The screw compactor may also fulfill the function of the pump or of the high-density solids pump. In one embodiment, the screw compactor may additionally be equipped with a pulverizing apparatus—similar to a meat grinder. For example, a rotating blade may be provided directly behind the outlet as the shredding machine. This rotating plate blade shreds the solids optionally present in that part of the liquid solution when they emerge from the outlet. Shredding and digestion of the solids distributed in the solution at the same time are therefore possible. The screw compactor may be made of a highly corrosion-resistant material, such as the aforementioned "Hastelloy C" alloy.

In an alternative embodiment of the method, the additional vessel is a housing of a static mixture, wherein the oxygen or the gas mixture is supplied to the portion of the liquid solution, wherein the portion of the liquid solution together with the oxygen or the gas mixture is passed through the static mixer or at least one part of the static mixer under the oxygen partial pressure of 1 to 500 bar.

There are various possibilities for the buildup of the oxygen partial pressure. For example, the oxygen partial pressure may be built up due to the fact that the oxygen or the gas mixture is supplied to that part of the liquid solution and that part of the liquid solution is then put under pressure and compressed together with the oxygen or the gas mixture by means of an additional pump or nozzle. The oxygen or the gas mixture may be contained in the portion of the liquid solution in the form of gas bubbles.

It is also possible to put the oxygen or the gas mixture under an oxygen partial pressure of 1 to 500 bar by means of another pump and to supply the gas mixture to that portion of the liquid solution, such that the oxygen partial pressure is maintained in that part of the liquid solution or is reduced only to the extent that it is still 1 to 500 bar. The counterpressure required to maintain the oxygen partial pressure in the portion of the liquid solution can be generated by means of the pump or an additional pump. To supply the oxygen or gas mixture, the oxygen or gas mixture may be injected into the liquid stream of that portion of the liquid solution through one or more nozzles. The nozzle or nozzles may be arranged in the direction of flow downstream from the pump or the additional pump to create the counterpressure and upstream from the static mixer and/or in the housing of the static mixer. The oxygen or the gas mixture may be contained in that portion of the liquid solution in the form of gas bubbles.

A suitable velocity of flow, at which that portion of the liquid solution is passed through the static mixer, depends on the design of the static mixer. It is to be selected so that an intense mixing of that portion of the liquid solution with the oxygen or the gas mixture occurs in the static mixer. A suitable velocity of flow for this purpose is usually specified by the manufacturer of the static mixer. The static mixer may be made of a highly corrosion-resistant material, such as the aforementioned "Hastelloy C" alloy.

During or after reduction of the oxygen partial pressure acting upon that portion of the liquid solution or after that portion of the liquid solution has again been supplied to the remainder of the liquid solution, a gas which outgases out of that portion of the liquid solution or the liquid solution itself must be allowed to escape from an apparatus suitable for carrying out the process or it must be removed. If that portion of the liquid solution is supplied to the remainder of the liquid solution in the vessel, then the outgassing gas can escape into the atmosphere when the vessel is open toward the atmosphere or is closed with an excess pressure valve which prevents a pressure increase to 1 bar or more.

The present invention will now be explained in greater detail on the basis of an exemplary embodiment.

Figure 2:
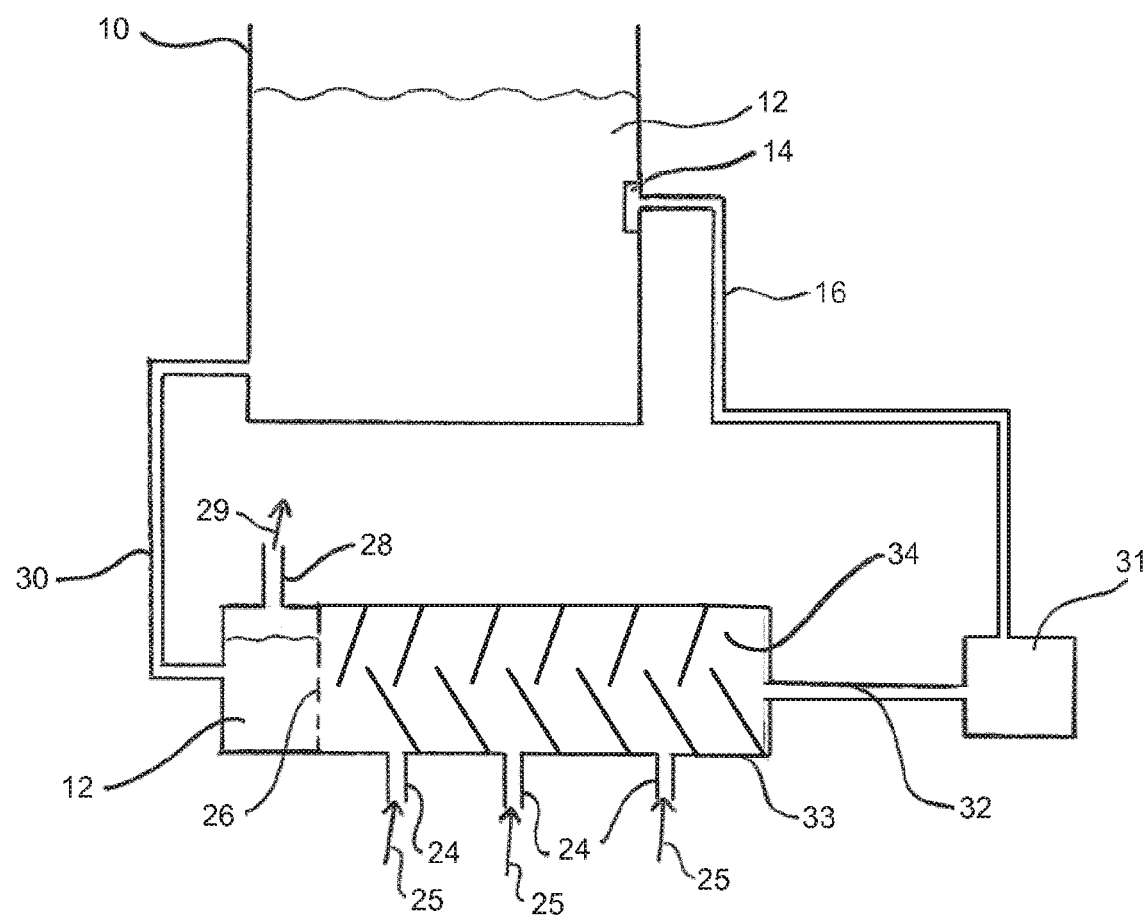

FIG. 1 shows a schematic diagram of an apparatus suitable for carrying out the process and FIG. 2 shows a schematic diagram of an alternative apparatus suitable for carrying out the process.

FIG. 1 shows a vessel 10 with a liquid solution 12 contained therein. The liquid solution 12 contains the catalyst and an alpha-hydroxyaldehyde, an alpha-hydroxycarboxylic acid, a carbohydrate, a glycoside or a polymer having a carbon chain with at least one OH group bound repeatedly to the carbon chain as a substituent and/or with an O, N or S atom occurring repeatedly in the carbon chain. The liquid solution is regulated at a temperature above 70° C. and below 120° C. An outlet line 16 with a filter 14 connected in front of it for removing a portion of the liquid solution 12 is provided on the vessel 10. A portion of the liquid solution goes through the outlet line 16 into the housing 18 of the screw compactor, where the screw compactor 20 driven by the drive 22 by means of the driveshaft 23 compresses that portion of the liquid solution 12 introduced into the housing 18 of the screw compactor with the air 25 introduced into it through the air inlet connection 24. That portion of the liquid solution 12 is pressed against the perforated mask 26. In doing so, an oxygen partial pressure of definitely more than 1 bar is built up in the screw compactor. The pressure depends on the resistance with which the perforated mask 26 opposes that portion of the liquid solution 12 and on the design of the screw compactor, in particular the pitch of the compressor screw 20 and the rotational speed at which the compressor screw 20 is rotated by the drive 22. Downstream from the perforated mask 26, that portion of the liquid solution 12 collects at a reduced oxygen partial pressure, wherein outgassing gas 29 can escape through the vent connection 28. That portion of the liquid solution 12 then passes through the inlet line 30 back to the remainder of the liquid solution 12 in the vessel 10. To do so, that portion of the liquid solution 12 can be conveyed through the inlet 30 by means of a pump (not shown here).

FIG. 2 shows a vessel 10 with liquid solution 12 contained therein. The liquid solution 12 contains the catalyst and an alpha-hydroxyaldehyde, an alpha-hydroxycarboxylic acid, a carbohydrate, a glycoside or a polymer containing a carbon chain having at least one OH group bound repeatedly as a substituent to the carbon chain and/or having an O, N or S atom occurring repeatedly in the carbon chain. The liquid solution is regulated at a temperature above 70° C. and below 120° C. An outlet line 16 with a filter 14 connected upstream for removing a portion of the liquid solution 12 is provided on the vessel 10. That portion of the liquid solution 12 enters the pump 31 through the outlet line 16 and goes from there through the connecting line 32 at an elevated pressure into the static mixer 34. Air 25 is introduced at an oxygen partial pressure of 1 to 500 bar into the static mixer through air inlet connection 24 in the housing 33 of the static mixer 34 and becomes mixed there with that portion of the liquid solution flowing in through the static mixer 34. An oxygen partial pressure of 1 to 500 bar is maintained in the static mixer 34 by means of the pump 31. That portion of the liquid solution 12 is pressed against the perforated mask 26. The oxygen partial pressure in the static mixer 34 depends on the pressure and the resistance built up by the pump 31 and on the resistance with which the perforated mask 26 opposes that part of the liquid solution 12. Behind the perforated mask 26, that portion of the liquid solution 12 collects at a reduced oxygen partial pressure, wherein outgassing gas 29 can escape through the vent connection 28. That portion of the liquid solution 12 then passes through the inlet line 30 back to the remainder of the liquid solution 12 in the vessel 10. To do so, that portion of the liquid solution can be conveyed through the inlet line 30 by means of a pump (not shown here).

LIST OF REFERENCE NUMERALS

10 vessel
12 liquid solution
14 filter
16 outlet line
18 housing of a screw compactor
20 compressor screw
22 drive
23 driveshaft
24 air inlet connection
25 air
26 perforated mask
28 degassing connection
29 gas
30 inlet line
31 pump
32 connecting line
33 housing of a static mixer
34 static mixer

What is claimed is:

1. A method for catalytic generation of formic acid at an oxygen partial pressure of less than 1 bar and regeneration of the catalyst used in this process, wherein a polyoxometallate ion of the general formula $[PMo_xV_yO_{40}]^{n-}$, which serves as the catalyst, is brought in contact with an alpha-hydroxyaldehyde, an alpha-hydroxycarboxylic acid, a carbohydrate, a glycoside or a polymer containing a carbon chain with at least one OH group bound as a repeatedly occurring substituent to the carbon chain and/or an O, N or S atom occurring repeatedly in the carbon chain in a liquid solution in a vessel, at a temperature above 70° C. and below 120° C., wherein $6 \leq x \leq 11$ and $1 \leq y \leq 6$ and $3 < n < 10$ and $x+y=12$, wherein n, x and y each denote an integer, wherein the catalyst thereby reduced is returned to its starting state by oxidation, wherein the contacting takes place in the vessel at an oxygen partial pressure of less than 1 bar, wherein a portion of the liquid solution is discharged from the vessel for oxidation of the catalyst, then is exposed to oxygen or a gas mixture containing oxygen at an oxygen partial pressure of 1 to 500 bar and next is fed back to the remainder of the liquid solution, wherein the oxygen partial pressure in the vessel is always kept below 1 bar, wherein the oxygen partial pressure acting on that portion of the liquid solution is lowered from 1 to 500 bar to less than 5 bar before that portion of the liquid solution is fed back to the remainder of the liquid solution.

2. The method according to claim 1, wherein the alpha-hydroxyaldehyde, the alpha-hydroxycarboxylic acid, the carbohydrate, the glycoside or the polymer is present in the liquid solution in the form of solids distributed therein.

3. The method according to claim 1, wherein the polymer is a polyester, a polyamine or a polyamide.

4. The method according to claim 1, wherein the contacting takes place at atmospheric pressure in the vessel, wherein the gas pressure in the vessel is always kept at atmospheric pressure.

5. The method according to claim 1, wherein that portion of the liquid solution is discharged continuously from the vessel, oxidized at an oxygen partial pressure of 1 to 500 bar and then fed continuously back to the remainder of the liquid solution.

6. The method according to claim 4, wherein the oxidation is carried out continuously.

7. The method according to claim 1, wherein that portion of the liquid solution is cooled before being exposed to the oxygen or the gas mixture and then is exposed to the oxygen partial pressure of 1 to 500 bar at a temperature of at most 95° C.

8. The method according to claim 1, wherein that portion of the liquid solution is conveyed by means of at least one pump or a high-density solids pump.

9. The method according to claim 1, wherein that portion of the liquid solution is exposed to the oxygen partial pressure of 1 to 500 bar in an additional vessel.

10. The method according to claim 9, wherein the oxygen or the gas mixture is fed to that portion of the liquid solution, the additional vessel is a housing of a screw compactor, and the oxygen partial pressure is built up by the fact that that portion of the liquid solution is compressed together with the oxygen or the gas mixture by means of the screw compactor.

11. The method according to claim 9, wherein the additional vessel is a housing of a static mixer, wherein the oxygen or the gas mixture is fed to that portion of the liquid solution, wherein that portion of the liquid solution is passed together with the oxygen or the gas mixture under the oxygen partial pressure of 1 to 500 bar at least through a portion of the static mixer.

12. The method according to claim 1, wherein the oxygen partial pressure acting upon that portion of the liquid solution is reduced from 1 to 500 bar to less than 1 bar before that portion of the liquid solution is fed back to the remainder of the liquid solution.

13. The method according to claim 1, wherein during or after the reduction in the oxygen partial pressure acting upon that portion of the liquid solution or after that portion of the liquid solution has been fed back to the remainder of the liquid solution, gas which has outgassed from that portion of the liquid solution or the liquid solution, is allowed to escape or is removed from an apparatus in which the method is carried out.

14. The method according to claim 1, wherein the polymer is a polymer without a plasticizer.

15. The method according to claim 1, wherein $n=3+y$.

16. The method according to claim 1, wherein that portion of the liquid solution is cooled before being exposed to the oxygen or the gas mixture and then is exposed to the oxygen partial pressure of 1 to 500 bar at a temperature of at most at most 85° C.

17. The method according to claim 1, wherein that portion of the liquid solution is cooled before being exposed to the oxygen or the gas mixture and then is exposed to the oxygen partial pressure of 1 to 500 bar at a temperature of at most at most 75° C.

18. The method according to claim 3, wherein the polymer is a polyhexamethylene adipamide.

19. The method according to claim 1, wherein the oxygen partial pressure acting upon that portion of the liquid solution is reduced from 1 to 500 bar to the oxygen partial pressure prevailing at atmospheric pressure before that portion of the liquid solution is fed back to the remainder of the liquid solution.

20. The method according to claim 9, wherein the additional vessel is a housing of a static mixer, wherein the oxygen or the gas mixture is fed to that portion of the liquid solution, wherein that portion of the liquid solution is passed together with the oxygen or the gas mixture under the oxygen partial pressure of 1 to 500 bar through the static mixer.

* * * * *